United States Patent [19]
Wallschlaeger

[11] Patent Number: 5,473,658
[45] Date of Patent: Dec. 5, 1995

[54] COMPUTER TOMOGRAPHY APPARATUS FOR CONDUCTING A SPIRAL SCAN OF AN EXAMINATION SUBJECT

[75] Inventor: Heinrich Wallschlaeger, Erlangen, Germany

[73] Assignee: Siemens Aktiengesellschaft, Munich, Germany

[21] Appl. No.: 233,989

[22] Filed: Apr. 28, 1994

[30] Foreign Application Priority Data

Jun. 24, 1993 [DE] Germany ............... 43 21 080.5

[51] Int. Cl.⁶ ............... A61B 6/03; G01N 23/08
[52] U.S. Cl. ............... 378/15; 378/901
[58] Field of Search ............... 378/15, 901

[56] References Cited

U.S. PATENT DOCUMENTS 5,073,911  12/1991  Ozaki et al. ............... 378/7
5,377,250  12/1994  Hu ............... 378/15
5,386,452  1/1995  Tohi ............... 378/146

FOREIGN PATENT DOCUMENTS

0504855A2  9/1992  European Pat. Off. .

*Primary Examiner*—David P. Porta
*Assistant Examiner*—David Vernon Bruce
*Attorney, Agent, or Firm*—Hill, Steadman & Simpson

[57] ABSTRACT

In a computer tomography apparatus which conducts a spiral scan, many images can be calculated quickly from spiral data, because data from the region of only one slice thickness are required. From an initial image $I_{l_r}(x)$ in the plane of a reference projection $l_r$ at a specific location along the system longitudinal axis and from an auxiliary image $I^d_{l_r+1}(x)$ the computer recursively calculates a new image $I_{l_r+1}(x)$ at the distance $d/N_{2\pi}$ from the initial image $I_{l_r}(x)$ according to the equation:

$$I_{l_r+1}(x) = I_{l_r}(x) - I^d_{l_r+1}(x)$$

whereby d is the slice thickness and $N_{2\pi}$ is the number of projections on the circumferential angle $2\pi$. The auxiliary image $I^d_{l_r+1}(x)$ was in turn also recursively acquired from its predecessor $I^d_{l_r}(x)$.

1 Claim, 1 Drawing Sheet

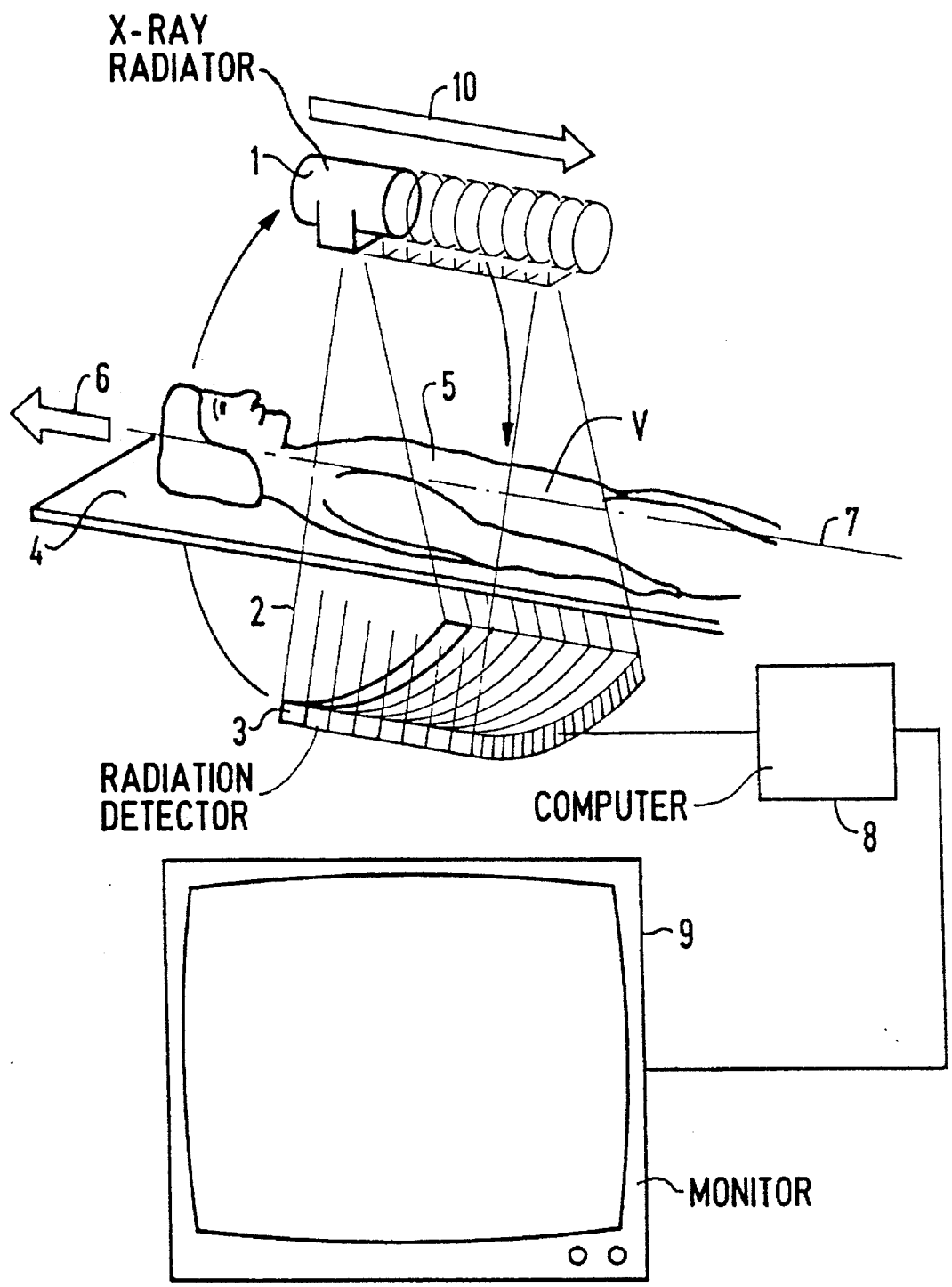

COMPUTER TOMOGRAPHY APPARATUS FOR CONDUCTING A SPIRAL SCAN OF AN EXAMINATION SUBJECT

BACKGROUND OF THE INVENTION

1. Field of the Invention

The present invention is directed to a computer tomography apparatus, and in particular to a computer tomography apparatus of the type for conducting a spiral scan.

2. Description of the Prior Art

The number of applications wherein many individual image must be prepared is increasing with the increasing significance of the spiral scan technique in computer tomography. Included among these applications is the production of three-dimensional reformations from many planar images or cine representations. The calculating and time outlay of an algorithm for the reformations becomes an important consideration of view under these circumstances. The number of convolution/back-projection operations required overall for calculating a desired plurality of images is considered a measure of this outlay.

When one wishes to calculate images at a distance of $N_s$ slice thicknesses d a spacing d/n with conventional spiral technique, i.e. $nN_s$ images, then $nN_sN_{2\pi}$ convolution/back-projection operations are required for this purpose ($N_{2\pi}$= number of projections onto $2\pi$). High values can be achieved dependent on the selection of the parameters. There is therefore great interest in methods that resolve this task quickly and without image quality losses.

European Application 0 504 855 discloses one possibility of making the image calculation faster on the basis of a recursive method for a spiral algorithm that requires data from the region of two entire slice thicknesses for the calculation of an image. The image quality, however, suffers thereby, particularly the resolution in the direction of the patient axis.

SUMMARY OF THE INVENTION

An object of the present invention is to provide a computer tomography apparatus having spiral scan for fast calculation of many images from spiral data such that data from the region of only one slice thickness are required.

The above object is achieved in accordance with the principles of the present invention in a computer tomography apparatus wherein a spiral scan of an examination subject is undertaken employing an x-ray radiator and a radiation detector, and wherein the output data from the radiation detector for only one slice thickness are employed for calculating an image of that thickness, the tomography apparatus including computer means for, from an initial image $I_{l_r}(x)$ in the plane of a reference projection $l_r$ at a specific location along the longitudinal axis of the system and from an auxiliary image $I^d_{l_r+1}(x)$, calculating a new image $I_{l_r+1}(x)$ at the distance $d/N_{2\pi}$ from the initial image $I_{l_r}(x)$ according to the equation: $I_{l_r+1}(x)=I_{l_r}(x)-I^d_{l_r+1}(x)$, wherein d is the slice thickness and $N_{2\pi}$ is the number of projections on the circumferential circle $2\pi$. The auxiliary image $I^d_{l_r+1}(x)$ was also recursively generated by the computer means from its predecessor $I^d_{l_r}(x)$.

The inventive apparatus employs a weighting algorithm, has good resolution in the direction of the patient axis, and supplies high contrast. Only two $N_sN_{2\pi}$ convolution/back-projection like operations are required in the apparatus for calculating the aforementioned $nN_s$ images. Compared to the conventional approach, this apparatus is thus faster by the factor n/2 for $2 < n \leq N_{2\pi}$.

DESCRIPTION OF THE DRAWINGS

The single FIGURE shows a block diagram of a computer tomography apparatus constructed and operating in accordance with the principles of the present invention.

DESCRIPTION OF THE PREFERRED EMBODIMENTS

The drawing shows an x-ray radiator 1 that emits a fan-shaped x-ray beam 2 that penetrates a patient 5 and is incident on a radiation detector 3 that is curved around the focus of the x-ray radiator 1 and is composed of a row of detector elements. A patient bed 4 on which the patient 5 lies is disposed between the x-ray radiator 1 and the radiation detector 3.

For scanning a volume of the patient 5, the patient bed 4 is adjusted by a predetermined dimension in the direction of the arrow 6, whereas the measuring unit formed of the x-ray radiator 1 and the detector 3 rotates around the system axis 7. The data thereby supplied from the detector elements of the radiation detector 3 are supplied to a computer 8 which calculates images of the patient 5 therefrom and effects their reproduction of the images on a viewing monitor 9. These images are computer tomograms of the scanned volume. Alternatively to the adjustment of the patient bed 4 in the direction of the arrow 6, the measuring unit can be adjusted in the direction of the arrow 10 for scanning a predetermined volume of the patient 5 even given a stationary patient bed 4.

Proceeding from an image $I_{l_r}(x)$ in the plane of a reference projection $l_r$ at a specific location along the system axis 7 and proceeding from an auxiliary image $I^d_{l_r+1}(x)$, a new image $I_{l_r+1}(x)$ at the distance $d/N_{2\pi}$ from the initial image is calculated in the computer 8 according to the following equation:

$$I_{l_r+1}(x)=I_{l_r}(x)-I^d_{l_r+1}(x)$$

The auxiliary image $I^d_{l_r+1}(x)$ describes the modifications effected overall by the advance and is in turn recursively calculated from the preceding auxiliary image $I^d_{l_r}(x)$ and two convolution/back-projection-like operations. The attenuation value of the $k^{th}$ channel of the $l^{th}$ projection of the spiral data set is referenced below as $S_{k,l}$. When the convolution/back-projection operator at the picture element x is referenced $O_k(x, \alpha)$ for the projection at the angle $\alpha$, then this recursion can be presented as follows:

$$I^d_{l_r+1}(x) = I^d_{l_r}(x) + 2 \sum_{k=1}^{N} O_k(x, \alpha_{l_r}) g_k^1 S_{k,l_r} -$$

$$2 \sum_{k=1}^{N} O_k(x, \alpha_{l_2(k)+l_r} + \pi) (g_k^2 S_{k,l_2(k)+l_r+N_\pi} + g_k^3 S_{k,l_2(k)+l_r-N_\pi})$$

The weightings $g^i_k$ are thereby essentially a measure for the distance between the participating attenuation value and the attenuation value complementary thereto. The following relationships are valid:

$$g_k^1 = \frac{2}{(1-f_k^2)N_\pi}, \; g_k^2 = \frac{1}{(1-f_k)N_\pi}, \; g_k^3 = \frac{1}{(1+f_k)N_\pi}$$

-continued whereby $$f_k = i\left(k - \frac{N+1}{2} + AM\right)\frac{2\Delta\beta}{\pi}$$

typically assumes values between −0.25 and +0.25. Further, $$l_2(k) = l + int(-f_k N_\pi)$$

is valid and $i_s$ indicates the rotational sense of the scan, N indicates the total number of channels, AM indicates the alignment of a projection and $\Delta\beta$ indicates the angular grid of the detector.

In order to begin the recursion, an image and an auxiliary image must be completely calculated. This occurs for the image according to the rule $$I_{lr}(x) = 2 \sum_{k=1}^{N} \sum_{l=l_2(k)+1}^{l_2(k)+N_{2\pi}} O_k(x, \alpha_{l+l_r-1} - \pi) \frac{l - 1 + (f_k - 1 + h_l)N_\pi}{(f_k + h_l)N_\pi} S_{k,l+l_r-N_\pi-1}$$

whereby $h_l=1$ for $l<N_\pi+1$ and $h_l=-1$ otherwise applies. The auxiliary image is calculated from $$I^d_{lr}(x) = 2 \sum_{k=1}^{N} \sum_{l=l_2(k)+1}^{l_2(k)+N_{2\pi}} O_k(x, \alpha_{l+l_r-1} - \pi) \frac{1}{(f_k + h_l)N_\pi} S_{k,l+l_r-N_\pi-1}$$

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising:

examination means, including a radiation source and a radiation detector, for conducting a spiral scan of an examination subject by rotating said radiation source and said radiation detector around a longitudinal axis through a plurality of projections, each projection generating output signals at said radiation detector corresponding to radiation incident on said detector attenuated by said examination subject, all of said output signals for a single slice of said examination subject comprising a data set;

computer means for calculating a new image $I_{lr+1}(x)$, using only a data set from a single slice, from an initial image $I_{lr}(x)$ in the plane of a referenced projection $l_r$ at a defined location along said longitudinal axis from an auxiliary image $I^d_{lr+1}(x)$ at a distance $d/N_{2\pi}$ from said initial image $I_{lr}(x)$ according to the equation:

$$I_{lr+1}(x) = I_{lr}(x) - I^d_{lr+1}(x)$$

and means for calculating said auxiliary image $I^d_{lr+1}(x)$ from its predecessor $I_{lr}(x)$, wherein d is the slice thickness and $N_{2\pi}$ is the number of projections on the circumferential angle; and means for displaying said image.

* * * * *